(12) United States Patent
Beychok et al.

(10) Patent No.: US 10,010,643 B1
(45) Date of Patent: Jul. 3, 2018

(54) APPARATUS FOR DISSOLVING A FRAGRANCE CARRIER

(71) Applicant: REMARKABLY WELL, INC, Atlanta, GA (US)

(72) Inventors: Alan M. Beychok, Atlanta, GA (US); Kathleen E. R. Huthmaker, McKinney, TX (US); Todd J. Huthmaker, McKinney, TX (US); Craig J. Cochran, Atlanta, GA (US); Adam D. Ambrecht, Kennesaw, GA (US)

(73) Assignee: REMARKABLY WELL, INC, Atlanta, GA (US)

( * ) Notice: Subject to any disclaimer, the term of this patent is extended or adjusted under 35 U.S.C. 154(b) by 0 days.

(21) Appl. No.: 15/691,281

(22) Filed: Aug. 30, 2017

(51) Int. Cl.
| | |
|---|---|
| *A62C 5/02* | (2006.01) |
| *A61L 9/12* | (2006.01) |
| *B05B 1/14* | (2006.01) |
| *A47K 3/28* | (2006.01) |
| *B05B 7/24* | (2006.01) |
| *A61L 9/012* | (2006.01) |
| *F16K 15/03* | (2006.01) |

(52) U.S. Cl.
CPC ............... *A61L 9/12* (2013.01); *A47K 3/281* (2013.01); *A61L 9/012* (2013.01); *B05B 1/14* (2013.01); *B05B 7/2462* (2013.01); *A61L 2209/13* (2013.01); *A61L 2209/15* (2013.01); *F16K 15/03* (2013.01)

(58) Field of Classification Search
CPC ... A61L 9/12; A61L 9/012; A61L 9/05; A61L 9/01; A47K 3/281; B05B 1/14; B05B 7/2462

USPC .... 239/6, 10, 34, 37, 38, 43, 273, 282, 289, 239/302, 310, 314, 379, 569; 4/596, 601, 4/605, 615, 661, 663, 903; 222/420, 422
See application file for complete search history.

(56) References Cited

U.S. PATENT DOCUMENTS

| | | | |
|---|---|---|---|
| 1,751,524 A | * | 3/1930 | Moss ...................... E03C 1/046 239/315 |
| 1,945,701 A | | 2/1934 | Pearl |

(Continued)

FOREIGN PATENT DOCUMENTS

| | | |
|---|---|---|
| JP | H038459 A | 1/1991 |
| WO | 0149421 A1 | 7/2001 |

(Continued)

OTHER PUBLICATIONS https://www.etsy.com/listing/497178378/lavender-shower-tablets-aromatherapy?utm_campaign=shopping_us_NaturalAcom_sfc_osa&utm_medium=cpc&utm_source=google&utm_custom1=0&utm_content=14309925&gclid=EAlalQobChMly-6RyOD_1QIVIoRpCh2ATAkJEAYYASABEgLWq_D_BwE , Aug. 29, 2017, 3 pgs.

(Continued)

*Primary Examiner* — Steven J Ganey
(74) *Attorney, Agent, or Firm* — Pearne & Gordon LLP (57) ABSTRACT

An apparatus for dissolving a fragrance carrier such as a shower tablet, including a fragrance carrier holder and a mount bracket supporting a water-holding reservoir and configured so that water in the reservoir or from the reservoir can contact and dissolve the fragrance carrier on the holder. The reservoir can be provided with a valve to at least partially control flow of water from the reservoir. The valve is preferably a flapper valve, a rotatable flow regulator valve, a poppet valve or a duckbill valve. A method of dissolving the fragrance carrier is also provided.

30 Claims, 12 Drawing Sheets

(56) References Cited

U.S. PATENT DOCUMENTS

| | | | |
|---|---|---|---|
| 1,973,319 A * | 9/1934 | Nelson | A47K 5/14 239/315 |
| 2,647,797 A | 8/1953 | Moss | |
| 2,986,340 A | 5/1961 | Webb | |
| 3,018,969 A | 1/1962 | Gentry | |
| 3,777,982 A | 12/1973 | Britton | |
| 4,211,368 A | 7/1980 | Legros et al. | |
| 4,580,751 A | 4/1986 | Panzer | |
| 5,025,919 A | 6/1991 | Brinker et al. | |
| 5,029,786 A | 7/1991 | Wu | |
| 5,238,915 A | 8/1993 | Fuwa et al. | |
| 5,957,387 A * | 9/1999 | Porta | B05B 1/1618 239/310 |
| 5,993,854 A | 11/1999 | Needleman et al. | |
| 6,006,374 A * | 12/1999 | Winnett | E03C 1/046 4/605 |
| 6,121,215 A | 9/2000 | Rau | |
| 6,244,778 B1 | 6/2001 | Chesbrough | |
| 6,550,735 B1 | 4/2003 | Zheng | |
| 6,557,782 B1 | 5/2003 | Urra | |
| 6,901,609 B2 | 6/2005 | Hill | |
| 7,093,775 B1 | 8/2006 | Bingham | |
| 7,207,464 B2 | 4/2007 | Brenner | |
| 7,220,436 B2 | 5/2007 | Rau | |
| 7,975,936 B2 | 7/2011 | Paoluccio | |
| 8,007,842 B2 | 8/2011 | Rau | |
| 8,028,933 B2 | 10/2011 | Friis | |
| 8,206,686 B2 | 6/2012 | Rau | |
| 8,566,972 B2 | 10/2013 | Vogtner et al. | |
| 8,820,660 B2 | 9/2014 | Ajagbe | |
| 8,955,536 B2 * | 2/2015 | Bell | C02F 1/50 422/263 |
| 9,085,006 B2 | 7/2015 | Wu et al. | |
| 9,200,667 B1 | 12/2015 | Hsu | |
| 2008/0146487 A1 | 6/2008 | O'Connor et al. | |
| 2009/0101733 A1 | 4/2009 | Popov et al. | |
| 2010/0040774 A1 | 2/2010 | Russell | |
| 2010/0199420 A1 | 8/2010 | Lee | |
| 2012/0283668 A1 | 11/2012 | Shalev | |
| 2014/0001027 A1 | 1/2014 | Balass | |
| 2014/0315719 A1 | 10/2014 | Rau et al. | |
| 2015/0053790 A1 | 2/2015 | Hanna et al. | |
| 2016/0243565 A1 | 8/2016 | Batista | |
| 2016/0287471 A1 | 10/2016 | Urfig | |
| 2016/0354306 A1 | 12/2016 | Rau et al. | |

FOREIGN PATENT DOCUMENTS

| | | | |
|---|---|---|---|
| WO | 2005063104 A1 | 7/2005 | |
| WO | 2010093947 A2 | 8/2010 | |

OTHER PUBLICATIONS http://www.ulta.com/luxe-aromatherapy-shower-tablets?productId=xlslmpprod15541099&sku=2503770&cmpid=PS_Non!google!Product_Listing_Ads&cagpspn=pla&CATCI=aud-297352281988:pla-297761130689&CAAGID=39172131008&CAWELAID=330000200001096929&catargetid=330000200001152683&cadevice=c&gclid=EAIaIQobChMIy-6RyOD_1QIVIoRpCh2ATAkJEAYYAiABEgJQjPD_BwE , Aug. 29, 2017, 2 pgs.
https://www.etsy.com/listing/509485540/small-bath-bomb-shower-tablet-orange?utm_campaign=shopping_us_HandmadeBeautyByLu_sfc_osa&utm_medium=cpc&utm_source=google&utm_custom1=0&utm_content=14926788&gclid=EAIaIQobChMIy-6RyOD_1QIVIoRpCh2ATAkJEAYYBSABEgIQRvD_BwE , Aug. 29, 2017, 3 pgs.
https://www.etsy.com/listing/269884683/shower-steamers-shower-fizzies-shower?gpla=1&gao=0&utm_campaign=shopping_us_BathThymeBoutique_sfc_osa&utm_medium=cpc&utm_source=google&utm_custom1=0&utm_content=11179150&gclid=EAIaIQobChMIy7au1OH_1QIVkDONCh32ywGwEAQYCCAB-EgITBfD_BwE , Aug. 29, 2017, 4 pages.
https://www.etsy.com/listing/514028380/menthol-shower-tablets?gpla=1&gao=0&utm_campaign=shopping_us_PrettiesByJudi_sfc_osa&utm_medium=cpc&utm_source=google&utm_custom1=0&utm_content=7095078&gclid=EAIaIQobChMIy7au1OH_1QIVkLXACh32ywGwEAQYCy-ABEgKIR_D_BwE , Aug. 29, 2017, 3 pages.
https://www.etsy.com/listing/273505698/shower-steamer-shower-bombs-shower-melts?gpla=1 &gao=1 &utm_campaign=shopping_us_FizzleSoap_sfc_osa&utm_medium=cpc&utm_source=google&utm_custom1=0&utm_content=12272935&gclid=EAIaIQobChMIy7au1OH_1QIVkLXACh32ywGwEAQYDi-ABEgK8bPD_BwE , Aug. 29, 2017, 7 pages.
https://www.bedbathandbeyond.com/store/product/aura-cacia-reg-3-count-aromatherapy-shower-tablets-in-relaxing-lavender/1017847767?skuId=17847767&mcid=PS_googlepla_nonbrand_beautywellness_online&product_id=17847767&adtype=pla_multichannel&product_channel=online&adpos=1o4&creative=43742630269&device=c&matchtype=&network=g&gclid=EAIaIQobChMIy-6RyOD_1QIVIoRpCh2ATAkJEAYYBCABEgJPUD_BwE , Aug. 29, 2017, 3 pages.
https://www.iherb.com/pr/Aromatherapaes-De-Stress-Spa-Shower-Tablets-Neroli-Chamomile-6-Aromatherapy-Tablets-8-oz-23-g-Each/66701?ccode=us&currcode=USD&langcode=en-US&gclid=EAIaIQobChMIy7au1OH_1QIVkLXACh32-ywGwEAQYCSABEgJWy_D_BwE , Aug. 29, 2017, 2 pages.
http://www.smallflower.com/patisserie-de-bain/lavender-bath-melt-45g-bath-tablets-10071098?utm_source=google&utm_medium=cpc&utm_campaign=sidecar&adpos=1o10&scid=scplp10071098&sc_intid=10071098&—gclid=EAIaIQobChMIy7au1OH_1QIVkLXACh32ywGwEAQYCi-ABEgKhefD_BwE , Aug. 29, 2017, 1 page.
Ulta Inc., Aromatherapy Shower Tablets, Aug. 9, 2017, 4 pages.
OnZen, OnZen Premium Shower Head, Aug. 29, 2017, 5 pages.
OPUS International LLC, Luxury Shower Head—Aroma Sense, Aug. 29, 2017, 4 pages.
Sigex Limited (HK), Cyclone Spa—Mineral Spa Shower System, Aug. 29, 2017, 2 pages.
Steam Spa, SteamSpa Steamhead with Aromatherapy Reservoir, Aug. 29, 2017, 4 pages.
https://www.etsy.com/listing/293287467/aromatherapy-shower-steamers?ref=pr_shop , Aug. 29, 2017, 3 pages.
http://www.ebay.es/itm/SPA-HOT-TUB-SPAZAZZ-AROMA-THERAPY-EFFERVESCENT-TABLETS-BOX-OF-12-/251902295552 , Aug. 29, 2017, 1 page.
Top Shelf Lacquer, Shower Bombs—Eucalyptus & Menthol, Aug. 29, 2017, 2 pages.

* cited by examiner

APPARATUS FOR DISSOLVING A FRAGRANCE CARRIER

FIELD OF THE INVENTION

The present invention relates to an apparatus for dissolving a fragrance carrier, preferably a shower tablet, in a shower or bath.

DESCRIPTION OF RELATED ART

US 2008/0146487 A1 teaches a tablet about the size of a small hockey puck which is thrown into the bathtub or onto the floor of a shower stall. The bath water or water from the shower head dissolves the tablet and releases aroma and fragrances. Typically, the tablet is effervescent. Bath bombs are also known, which are placed in bathwater to add essential oils, scent, bubbles and color to the bathwater. There is a need for an apparatus which holds the fragrance carrier and keeps it out of the bathwater and off the floor of the shower stall, so it won't be stepped or sat on and so that dissolution of the fragrance carrier can preferably be controlled and/or slowed down.

SUMMARY OF THE INVENTION

An apparatus for dissolving a fragrance carrier, the apparatus comprising a mount bracket, a water-holding reservoir and a fragrance carrier holder, the water-holding reservoir being supported by the mount bracket, the fragrance carrier holder being provided in association with the water-holding reservoir such that (a) water in the water-holding reservoir can contact and dissolve a fragrance carrier located on the fragrance carrier holder, the fragrance carrier holder being located inside the water-holding reservoir, or (b) water can flow from the water-holding reservoir to contact and dissolve a fragrance carrier located on the fragrance carrier holder. The water-holding reservoir preferably has one or more drain openings at a bottom of the water-holding reservoir. A method for dissolving a fragrance carrier is also provided.

DETAILED DESCRIPTION OF PREFERRED EMBODIMENTS OF THE INVENTION

In the description that follows, when a preferred range, such as 5 to 25 (or 5-25) is given, this means preferably at least 5 and, separately and independently, preferably not more than 25.

With reference to FIGS. 1 and 4-6, there is shown a preferred embodiment of the invention, that is, an apparatus 2 (preferably made of plastic or metal) for dissolving a fragrance carrier. In the present invention, the fragrance carrier carries the fragrance and releases the fragrance into the shower or bath area as the fragrance carrier dissolves in water. The fragrance carrier is preferably a shower tablet 48 as known in the art, preferably a fragranced shower tablet or an effervescent or non-effervescent shower tablet or an aromatherapy shower tablet as known in the art, which has a composition as known in the art, for example comprising sodium bicarbonate, citric or adipic acid, maltodextrin and fragrance such as perfume. As known in the art, when water contacts the shower tablet, it fizzes or effervesces and releases the fragrance into the shower and surrounding bathroom, energizing, refreshing and/or calming the user; the fragrance can also be directed for enhancing or transforming the mood of the user. Optionally, the shower tablet can be a shower tablet for therapeutic purposes including but not limited to sinus decongestion via vapors released from the shower tablet. The shower tablet 48 is preferably about 1 to 2, or about 1.5, cm high and 4-6 cm in diameter and weighs about 26-40 g. When the tablet 48 is centered in the cup 8, the distance from the perimeter of the tablet to the front face of the vertical portion (e.g., 9c1) of the ribs is about 1-3 mm, and to the wall 61 is about 2-5 mm.

Figure 24:
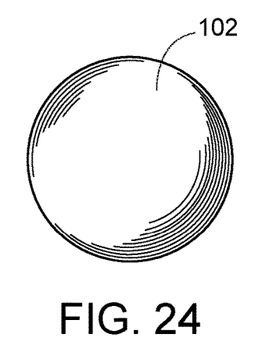
FIG. 24 is a schematic top view illustration of an alternative embodiment of a fragrance carrier.
Figure 25:
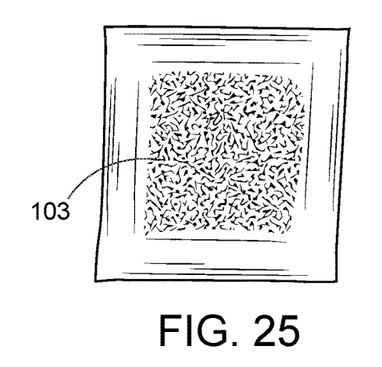
FIG. 25 is a schematic top view illustration of an alternative embodiment of a fragrance carrier inside a filter bag.
Figure 26:
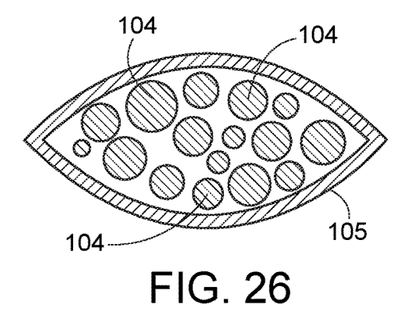
FIG. 26 is a schematic cross-sectional side view of an alternative embodiment of a fragrance carrier inside a mesh bag.
Figure 27:
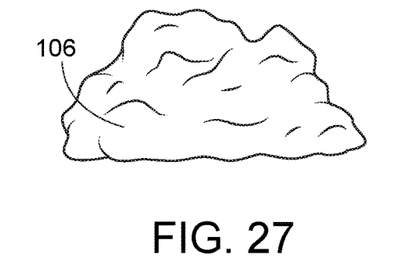
FIG. 27 is a schematic side view illustration of an alternative embodiment of a fragrance carrier.
Figure 28:
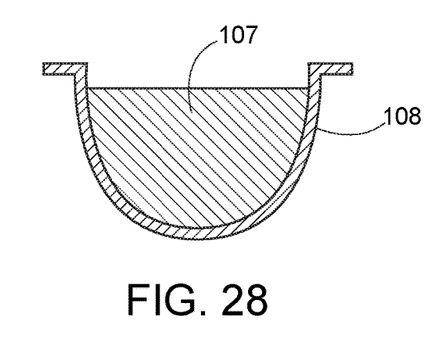
FIG. 28 is a schematic cross-sectional side view of an alternative embodiment of a fragrance carrier in a cup.

Alternatively, the fragrance carrier can be the same or similar composition as a shower tablet described above, but in the shape of a ball 102 (see FIG. 24) or any other shape or size (powder, small granules, pellets, etc.) or the fragrance carrier can be in the form or shape of a powder or crystals or fragrance salts or small granules in a filter bag 103 (see FIG. 25) which is water-permeable material like a tea bag or sachet bag or fabric bag or the fragrance carrier can be larger granules 104 or pellets 104 or small balls 104 (e.g., 3-10 mm in diameter) in a plastic or fabric mesh bag 105 (FIG. 26), or the fragrance carrier can be a blob of gel 106 (FIG. 27) or a solid or gel 107 in a plastic cup 108 (FIG. 28).

Figure 1:
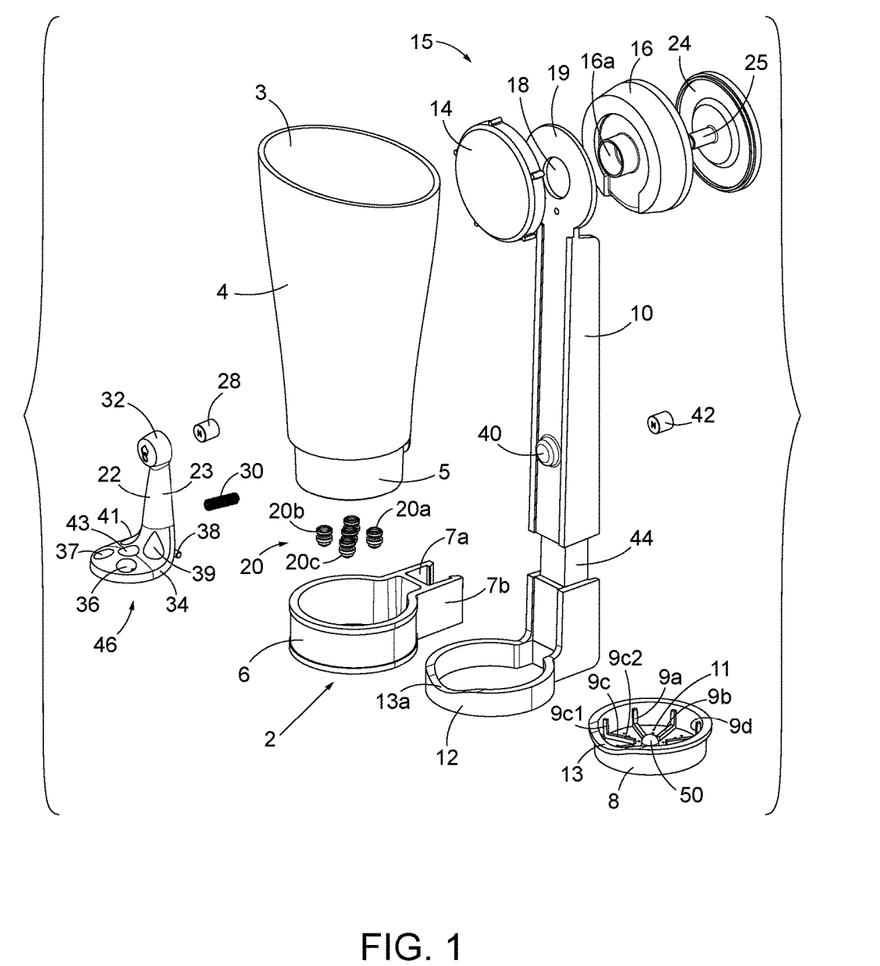
FIG. 1 is an exploded view of an apparatus according to an embodiment of the invention for dissolving a fragrance carrier.

The apparatus 2 comprises a water-holding reservoir 4 (preferably polycarbonate plastic), a mount bracket 10, a wall mount 15, a reservoir support bracket 6, a fragrance carrier holder or dissolving cup 8 and a fragrance carrier holder support bracket or dissolving cup support bracket 12. The mount bracket comprises the reservoir support bracket and the fragrance carrier holder support bracket or dissolving cup support bracket; all the brackets are preferably plastic or metal. The reservoir 4 is supported by the mount bracket 10 and has an opening 3 at the top and a narrowed portion 5 at the bottom to engage and seat in the reservoir support bracket 6. Alternatively, support bracket 6 can engage reservoir 4 higher up, such as half-way up reservoir 4, for example via a narrowed portion or via other attachment mechanism. Reservoir 4 is preferably shaped so that it is wider in the upper portion and narrower in the lower portion, or wider the higher it extends up from the bottom, as a funnel-shape, as shown in FIG. 1; this provides a water tower funnel effect, such that water pressure at the bottom is higher for a longer period than if the reservoir was narrower in the upper portion. The bottom of reservoir 4 can be sealed via a valve, such as valve 22, as described later. Support bracket 6 clips to mount bracket 10 at necked-down region 44 via snap arms or latching arms 7a, 7b. Alternatively, bracket 6 can be integrally molded with bracket 10 or attached via other means as known in the art.

Figure 12:
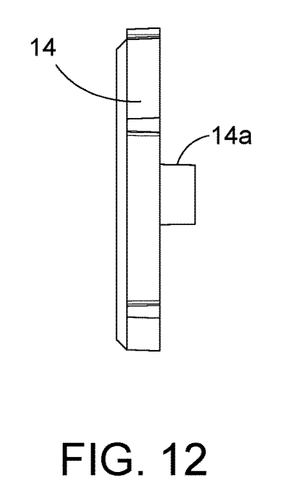
FIG. 12 is a side view of the knob 14.

Mount bracket 10 can be fixed or mounted in a shower stall or in or above a bathtub, preferably about 4-6 feet (122-183 cm) or about 5 feet (152 cm) above the floor, to a wall or a substantially vertical surface (e.g., tile or wall of a shower stall) via wall mount 15, which preferably comprises a knob 14, a mount housing 16, and a mount suction cup 24. The knob 14 has a hollow internally-threaded central post 14a (see FIG. 12) which extends through hole 18 in the top portion 19 of mount bracket 10, through opening 16a of mount housing 16, and around an externally-threaded post 25 of mount suction cup 24. Knob 14 is rotated to threadingly pull back the central portion of mount suction cup 24 so that mount suction cup 24 will adhere to the wall or tile via suction force, as is known in the art. Optionally, mount housing 16 can be made integrally with portion 19 of mount bracket 10.

Alternatively, instead of mount suction cup 24, there can be used a mount anchor 26 (see FIG. 2) comprising an externally-threaded post 27 (corresponding to post 25) and an adhesive surface 52 so that mount anchor 26 can adhesively adhere to the tile or wall or other surface. Other wall mounts as known in the art can be used to mount the mount bracket 10 on the wall, and the wall mount or any of its parts can optionally be integrally molded or unitary or one piece with the mount bracket.

Fragrance carrier holder support bracket or dissolving cup support bracket 12 can be integrally molded as part of mount bracket 10, or can be molded separately and clipped or otherwise fixed to mount bracket 10 as known in the art.

Figures 2, 3, 4:
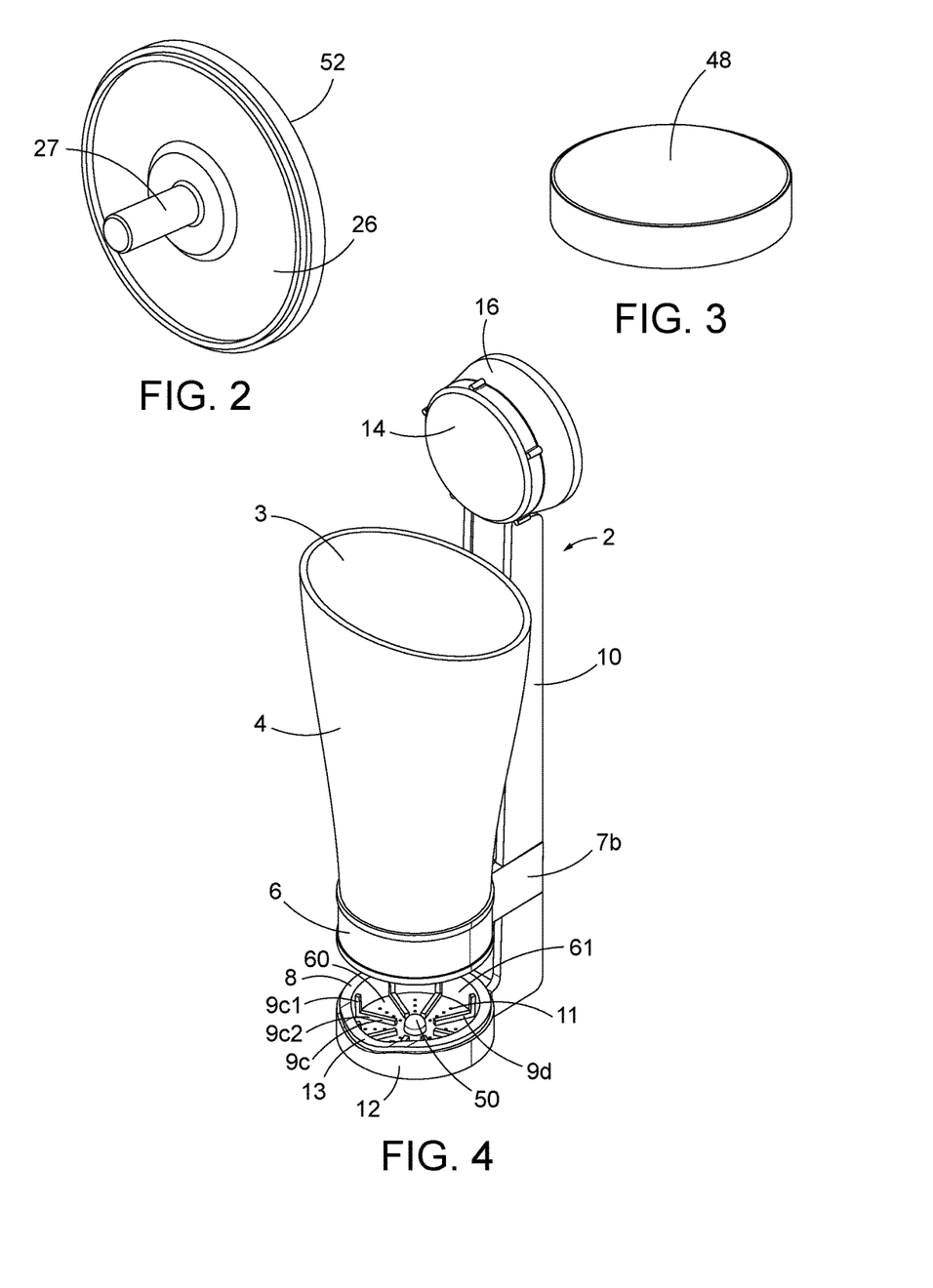
FIG. 2 is a perspective view of a mount anchor.
FIG. 3 is a perspective view of a fragrance carrier or shower tablet for use with the apparatus of FIGS. 1 and 4 and other apparatuses according to the invention.
FIG. 4 is a perspective view of the apparatus of FIG. 1 in an assembled and operating condition.
Figure 5:
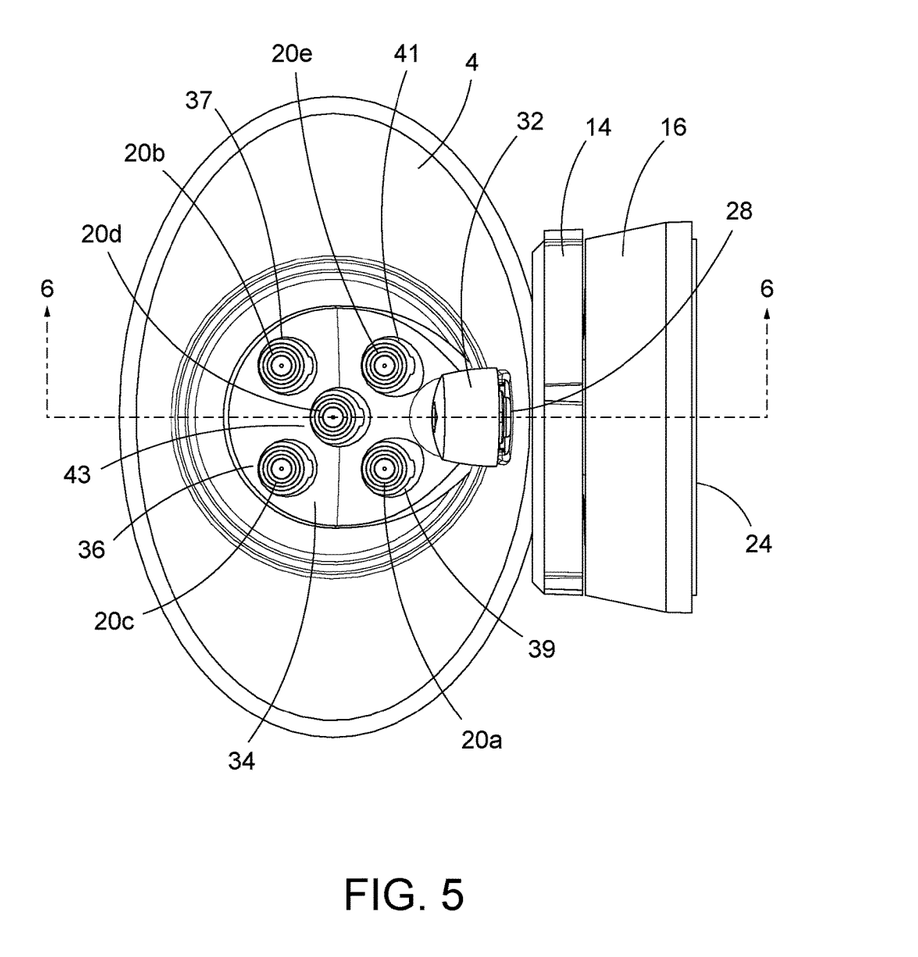
FIG. 5 is a top plan view of the apparatus of FIG. 4.
Figure 6:
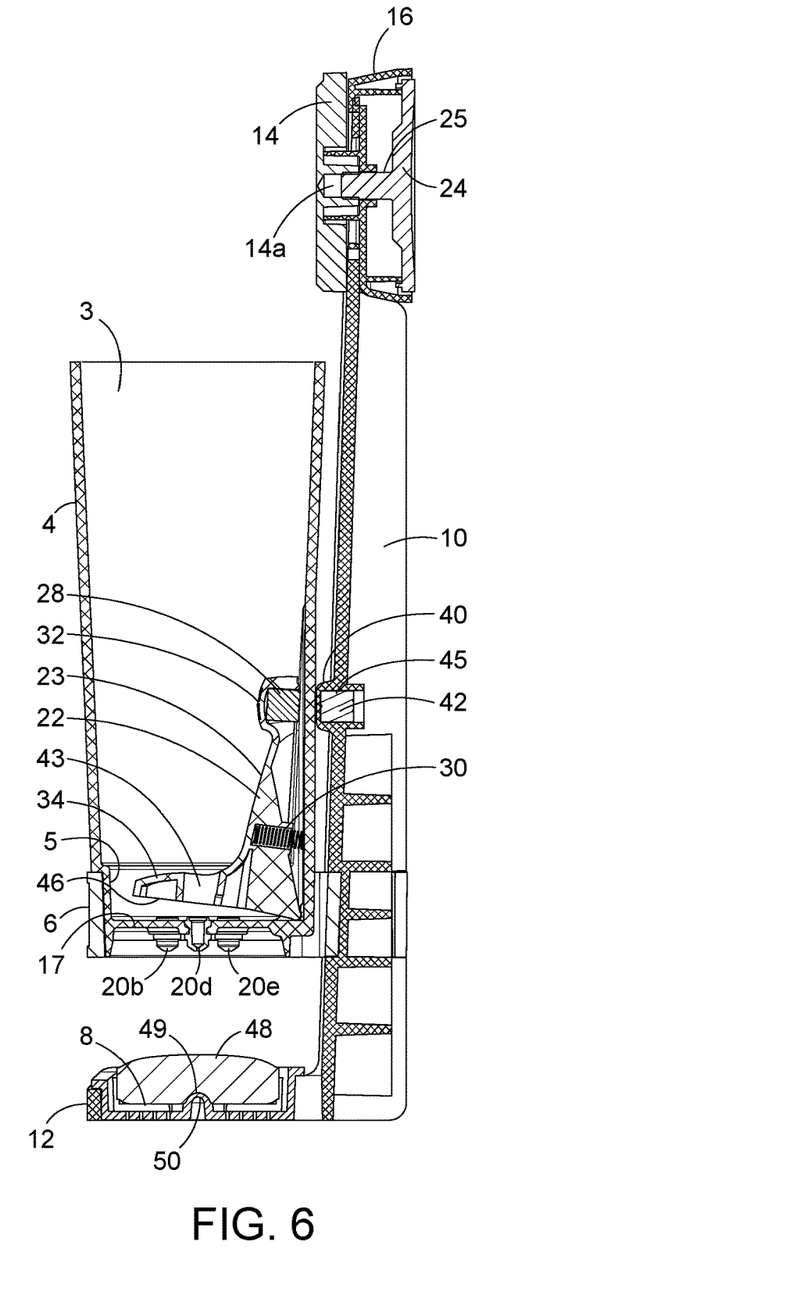
FIG. 6 is a cross-sectional view taken along line 6-6 of FIG. 5.

With reference to FIGS. 1, 4 and 6, the fragrance carrier holder or dissolving cup 8 is located beneath the bottom of the reservoir 4 and has a series of standoffs or ribs 9a, 9b, 9c, 9d and others. Each rib (e.g., rib 9c) has a horizontal portion (e.g., 9c2) adjacent the floor 60, and a vertical portion (e.g., 9c1) adjacent the inner perimeter wall 61 of the dissolving cup 8. The ribs keep the fragrance carrier or shower tablet 48 (see FIGS. 3 and 6) spaced apart from the floor 60 and wall 61 of the cup 8 so that more tablet 48 surface area is exposed to the dissolving action of the water. The floor 60 of cup 8 has a series of drain holes or openings 11 (preferably 1-3 mm) (the wall 61 can also have drain holes) and a central protrusion or dome or bump or post or knob 50 which engages a corresponding central cavity 49 (preferably having a shape corresponding to the exterior shape of the protrusion 50) on the bottom of the shower tablet 48. The protrusion 50/cavity 49 helps keep the tablet 48 centered in the cup 8 for more effective dissolution, even as the tablet 48 gets smaller. The dome shape of the protrusion 50/cavity 49 can alternatively be another ornamental shape, such as a cylindrical post, or a post having (in plan view) the shape of a triangle, square, rectangle, oval, star, polygon, bow tie, baseball bat, boomerang, baseball glove, etc.

Figure 19:
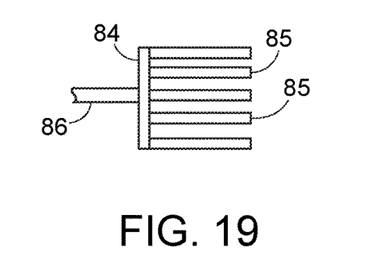
FIG. 19 is a schematic top view illustration of an alternative embodiment of a fragrance carrier holder.
Figure 20:
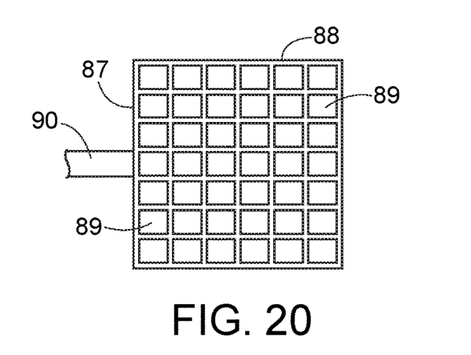
FIG. 20 is a schematic top view illustration of an alternative embodiment of a fragrance carrier holder.
Figure 21:
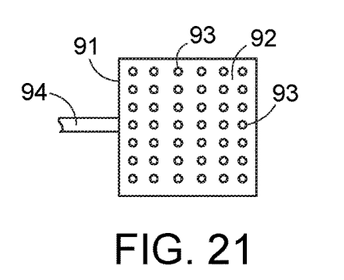
FIG. 21 is a schematic top view illustration of an alternative embodiment of a fragrance carrier holder.
Figure 22:
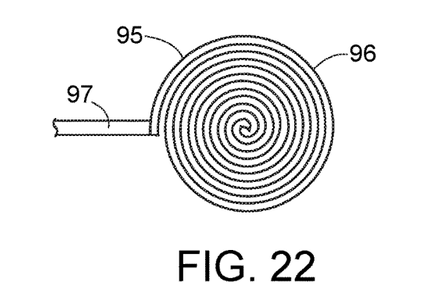
FIG. 22 is a schematic top view illustration of an alternative embodiment of a fragrance carrier holder.
Figure 23:
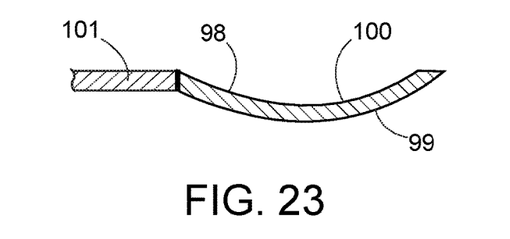
FIG. 23 is a schematic cross-sectional side view of an alternative embodiment of a fragrance carrier holder.

Cup 8 has a lip 13 which is lower than the rest of wall 61, to permit excess water to drain out; support bracket 12 has a corresponding lip 13a. Dissolving cup 8 is a preferred embodiment of a fragrance carrier holder (which is designed and effective to hold a fragrance carrier and permit it to be dissolved by water); other fragrance carrier holders can be used, such as shown in FIGS. 19-23, described as follows. FIG. 19 shows a fragrance carrier holder 84 having a series of prongs or fingers 85 for holding the shower tablet 48 or other fragrance carrier (such as described with reference to FIGS. 24-28). The fragrance carrier holder 84 is attached to the mount bracket 10 by a fragrance carrier holder support bracket, a portion of which is shown at 86; the rest of support bracket 86 is fixed to mount bracket 10 similar or the same as support bracket 12 is attached to mount bracket 10. FIG. 20 shows a fragrance carrier holder 87 comprising a grate 88 having a series of drain holes or drainage openings 89; a portion 90 of the fragrance carrier holder support bracket is also shown. A screen can be used in place of the grate. FIG. 21 shows a fragrance carrier holder 91 comprising a tray or shelf 92 which can have drainage perforations 93 or which can be unperforated; a portion 94 of the fragrance carrier holder support bracket is also shown. FIG. 22 shows a fragrance carrier holder 95 comprising a coil 96 (preferably metal or plastic) for holding the shower tablet 48 or other fragrance carrier; a portion 97 of the fragrance carrier holder support bracket is also shown. FIG. 23 shows a fragrance carrier holder 98 comprising a dish or cup 99 (which is preferably circular or rectangular in plan view and which can be perforated or non-perforated) which has a concave inner surface 100; a portion 101 of the fragrance carrier holder support bracket is also shown. All the fragrance carrier holders can be flat, or can be concave like fragrance carrier holder 98 to better hold the fragrance carrier; all the fragrance carrier holders can optionally have (a) a perimeter wall like perimeter wall 61 and (b) ribs or standoffs like ribs 9a, 9c, etc. A fragrance carrier holder that is sized to effectively hold a shower tablet is a tablet holder.

With reference to FIGS. 1, 5, 6 and 7, the reservoir 4 has a bottom or floor 17 through which extend one or more nozzles 20 (five nozzles are shown, but alternatively there can be 1, 2, 3, 4, 6, 7, 8, 9, 10 or more); these nozzles are drain openings. Before being added to the floor 17, the nozzle can be molded individually or in one or more groups where they are integrally or monolithically joined together via connecting or interconnected arms or similar. The nozzles 20 or nozzle group or groups can be assembled to or co-molded or overmolded with floor 17, which is preferably molded with the rest of the reservoir 4. Each nozzle 20 has a central bore, preferably 0.2-1.5, 0.3-1.2, 0.4-1, 0.5-0.8 or about 0.6, mm in diameter, through which the water in the reservoir 4 passes. Alternatively, different nozzles can have different diameter bores; for example, with 5 nozzles, 3 nozzles can have 0.6 mm bores and the other 2 can have 0.5 mm bores, to regulate volume of flow to different parts of a tablet 48 or other fragrance carrier. The drain holes (such as holes 11) in the cup 8 can have a diameter (and/or number of holes) which is a function of the diameter and number of nozzles 20 in the reservoir 4, so that the amount of water held in the cup 8 (inflow minus outflow) is controlled or regulated, to control the amount of water retained and surrounding the tablet 48 or other fragrance carrier, to control or regulate the dissolution rate. The nozzles can also be openings through the floor 17.

The water-holding reservoir is preferably provided with a valve, preferably a valve selected from the group consisting of flapper valves, rotatable flow regulator valves, poppet valves and duckbill valves.

Figure 7:
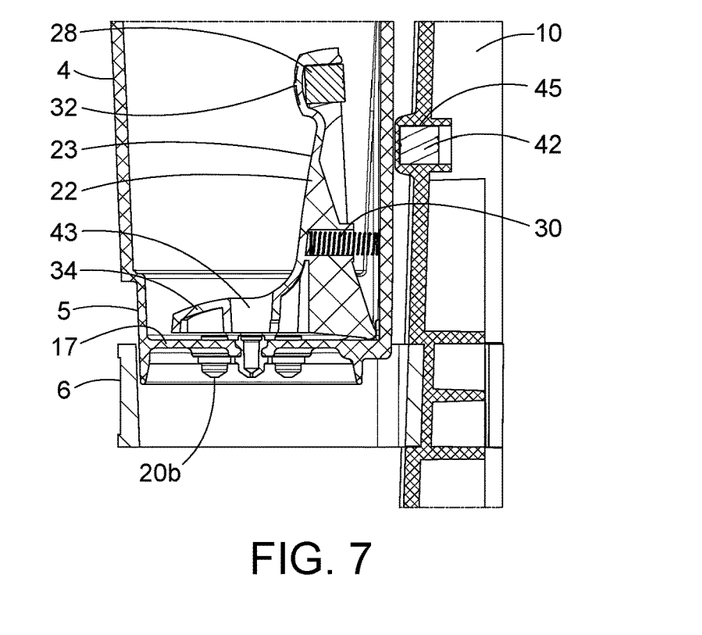
FIG. 7 is a view similar to FIG. 6, but where the bottom or narrowed portion 5 of the reservoir 4 has not been put into the reservoir support bracket 6 and the valve 22 is closed.
Figure 8:
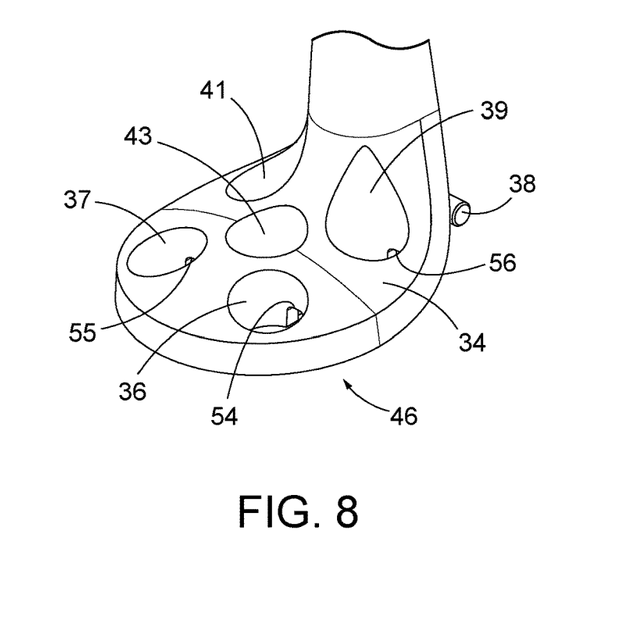
FIG. 8 is a perspective view of the foot 34 of the valve 22.

With reference to FIGS. 1 and 5-11, there is shown a flapper valve 22 comprising a central portion 23, a flapper foot or valve foot 34 and a pivot 38. A valve magnet housing 32 is provided at the top of the central portion 23; a valve magnet or first magnet 28 is constrained or fixed in the housing 32. A plurality of bores 36, 37, 39, 41, 43 are provided in valve foot or flapper foot 34. A resilient and/or elastomeric (or hard or rigid plaster) valve membrane 46 (preferably about 1-2 mm thick) is fixed to the bottom of the foot 34; the top of each nozzle 20 is preferably flat (see FIGS. 1, 7 and 8) so that when the foot 34 is in the closed position as shown in FIG. 7, the valve membrane 46 closes the top of the central bore of each nozzle 20.

Figure 9:
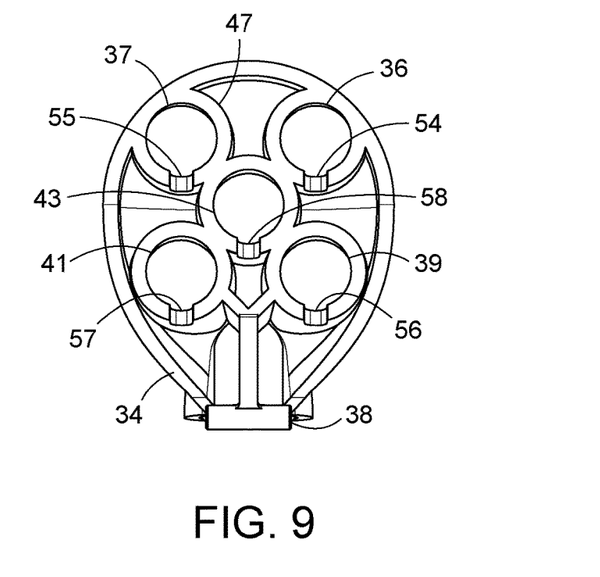
FIG. 9 is a bottom plan view of the valve 22.
Figure 10:
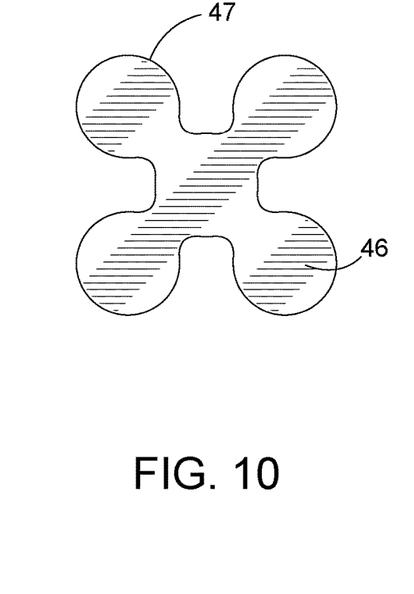
FIG. 10 is a top plan view of a valve membrane.

At the bottom of each bore 36, 37, 39, 41, 43 (and above the valve membrane 46) there is a respective drain hole 54, 55, 56, 57, 58 which drains water from the bore when the foot 34 is in the open position as shown in FIG. 6. As shown in FIGS. 9-10 and as indicated by the location of valve membrane perimeter 47 in FIGS. 9-10, the valve membrane 46 is sized so that it covers the bottom of each bore 36, 37, 39, 41, 43 and an additional 1-3 mm, to facilitate good sealing with the top of each nozzle 20.

Figure 11:
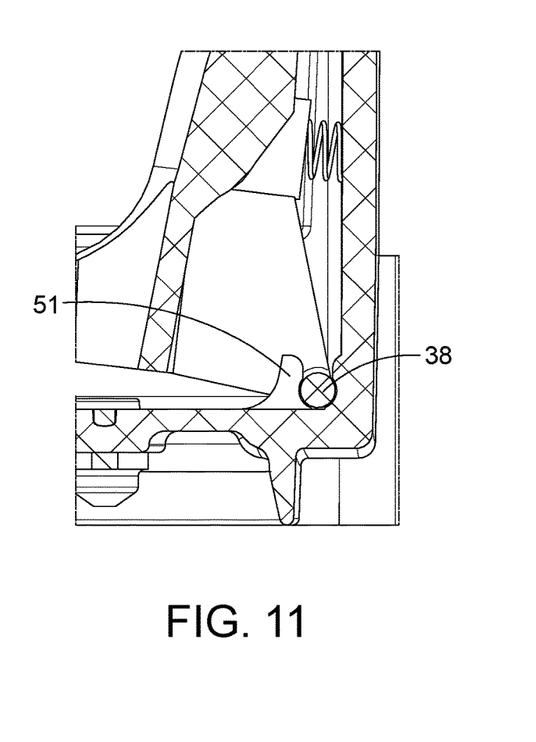
FIG. 11 is a view similar to a central portion of FIG. 6, showing the pivot and pivot seating.

As shown in FIG. 11, pivot 38 snaps into pivot seating 51 so that flapper valve 22 is fixed inside and near the bottom of reservoir 4 and can rotate clockwise/counterclockwise with reference to FIGS. 6, 7, 11. With reference to FIGS. 6-7, valve 22 is spring-biased or spring-loaded such that, when the reservoir 4 is removed from the reservoir support bracket 6 (such as for refilling with water), the spring 30, which is fixed in position between the valve 22 and the wall of reservoir 4, urges the valve 22 to rotate until it closes and clampingly seals, via membrane 46, the central bore at the top of each nozzle 20.

In operation, the shower tablet 48 or other fragrance carrier is positioned in the dissolving cup 8, which is positioned in the dissolving cup support bracket 12. When the user wants to take a shower or bath, the user removes the reservoir 4 from the support bracket 6. The spring 30 then biases the valve 22 to rotate until the membrane 46 presses against the tops of the nozzles 20 and closes them. The user then fills or at least partially fills (such as from the shower head) the reservoir 4 with water (preferably warm or hot), which can't escape because the valve 22 is closed. The user then seats or mounts the bottom or narrowed portion 5 of the reservoir 4 in or on the support bracket 6. In this position (see FIG. 6), the magnet 28, which is fixed in housing 32, is magnetically attracted, due to spatial proximity, to the mount bracket magnet or second magnet 42, which is constrained or fixed in a cavity 45 (behind a nesting bulge 40) located in the mount bracket 10. The magnetic attraction of the magnets 28, 42 overcomes the resistance of the spring 30 and rotates valve 22 towards second magnet 42 (see FIG. 6) so that the foot 34 and membrane 46 lift off the nozzles 20, causing the foot 34 to open, opening the central bores of the nozzles 20 so that the water in the reservoir 4 can flow through the nozzles 20 and fall onto the fragrance carrier or tablet 48. The tablet 48 is dissolved primarily by the falling water and may also be partially dissolved by water accumulating in the dissolving cup 8. When the fragrance carrier is 93% dissolved, it is at least substantially dissolved. The water will slowly dissolve the tablet 48 or other fragrance carrier and release its fragrance into the air, providing aromatherapy to the user (this aromatherapy being known in the art). Water can drain through the drain holes 11 and go over the lips 13, 13a, falling into the bath or shower stall. Substantially all the water in the reservoir 4 will flow out; the water in the bores 36, 37, 39, 41, 43 will flow out (due to tilting) through the respective drain holes 54-58 (provided at the base of the flapper foot 34) and then out through the nozzles 20. Preferably the size of the tablet/fragrance carrier 48, the volume of the reservoir 4, the number of nozzles and the diameter of the bore in each nozzle are predetermined so that the tablet 48 completely dissolves shortly (about 10-30 seconds) before the water runs out; preferably the flow is such as to dissolve the tablet 48 in about 1-20 or 3-15 or 7-10 minutes.

The magnets are preferably neodymium or similar, due to the strength thereof. The reservoir 4 is sized to receive a shower tablet therein and preferably holds 0.5 to 1 or 1.5 liters of water and is 15 to 20 cm high, measured from the floor 17. The dissolving cup 8 is preferably 2 to 4 cm in diameter (measuring the diameter of the circle defined by the front faces of the vertical portions of the ribs 9a, 9b, etc. or, less preferably, measuring the diameter of the circle defined by the wall 61) and 0.5 to 1.5 cm high (measured from the tops of horizontal portions such as 9c2 or, less preferably, measured from the floor 60).

Assuming the valve 22 is closed and the reservoir 4 is fully seated in the support bracket 6, the distance between the magnets 28 and 42 is preferably about 1-3 or 1-2 or about 1.5 or about 2 cm.

Other flapper valves can be used, such as a flapper valve which is commonly used in a residential toilet, wherein, for example, the user can pull the chain to open the flapper foot of the flapper valve and then hook the chain, via a hook attached to the chain, on the rim of the reservoir 4 or elsewhere on the apparatus 2, to keep the flapper foot open.

Figure 13:
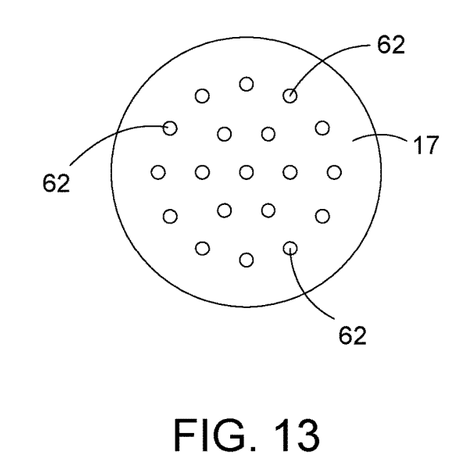
FIG. 13 is a top plan view of an alternative embodiment of the floor of the reservoir.

Alternatively, the apparatus 2 can be constructed without the presence of a valve such as valve 22. In this case, when the reservoir 4 is filled with water, water begins immediately to flow through the nozzles 20. This is less preferred, since water will flow out of the reservoir 4 as the user is filling the reservoir and transporting it to the bracket 10 and installing it in the support bracket 6, getting everything wet. In this embodiment, the nozzles 20 can even be omitted and small drain holes 62 can be provided directly in floor 17 of reservoir 4, as shown in FIG. 13. As noted, the dissolving cup 8 is provided in association with the reservoir 4 so that water can flow from the reservoir 4 to the dissolving cup 8 to dissolve a shower tablet or fragrance carrier in the cup 8.

Figure 14:
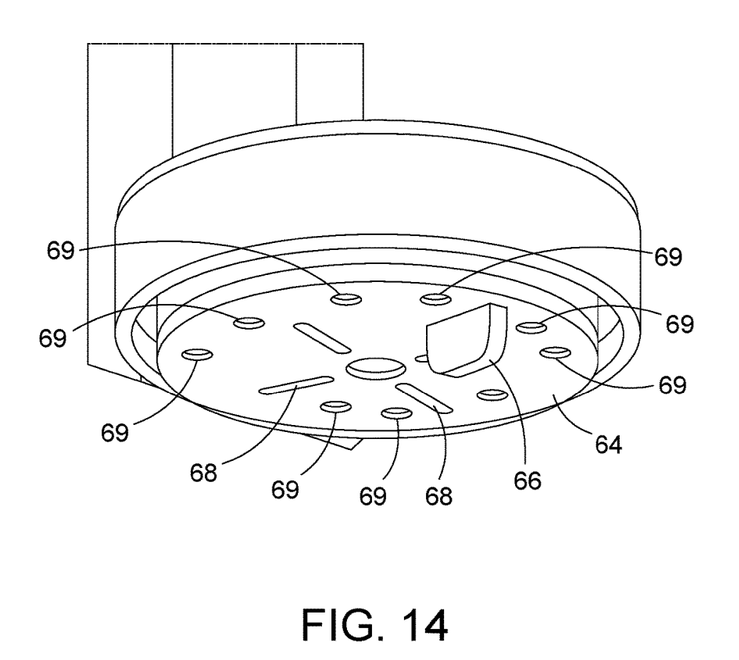
FIG. 14 is an alternative embodiment of a valve of the reservoir.

Alternatively, in place of valve 22, a rotatable flow regulator valve 64 (see FIG. 14) can be attached immediately beneath floor 17 (whether floor 17 has holes 62 or nozzles 20). Valve 64 is provided with drainage slots or openings 68 and/or drainage holes or openings 69 (located at predetermined positions) and a finger tab 66. In a first position or orientation, valve 64 blocks all holes 62, so no water flows. Then valve 64 is rotated via finger tab 66 to a second position, where the openings 68, 69 line up with some of the holes 62, so some water flows. Then valve 64 is rotated to a third position, where the openings 68, 69 line up with all the holes 62, so maximum flow is permitted. In this way, the volume of flow can be controlled or regulated. Less preferably, valve 64 can be fixed in position and non-rotatable, but reservoir 4 can be rotated by the user so that none or some or all of the holes 62 line up with the openings 68, 69. Other rotatable flow regulator valves known in the art can be used.

Figure 15:
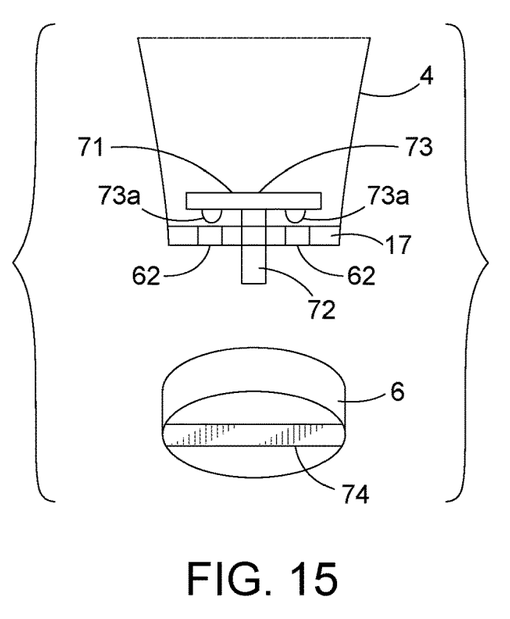
FIG. 15 is a schematic exploded view illustration of an alternative embodiment of a valve for the reservoir.

Alternatively, a poppet valve can be used. With reference to FIG. 15, the bottom or floor 17 of the reservoir 4 has a plurality of holes 62 (compare with FIG. 13). A spring-loaded poppet valve 71, having a post 72, is provided. A spring attached to the post 72 biases the cap 73 of the poppet valve 71 in the closed position, so that the knobs or bumps 73a plug or seal the holes 62. When the reservoir 4 is seated in the support bracket 6, the bottom of the post 72 contacts the center of a crosspiece 74 fixed at the bottom of the support bracket 6 and forces the cap 73 upwards, so that the spring is compressed and the valve 71 is opened and the holes 62 are unsealed and water can flow through. Perforations can also be provided at selected locations through the cap 73 and through the crosspiece 74. Other poppet valves known in the art can be used.

Figure 16:
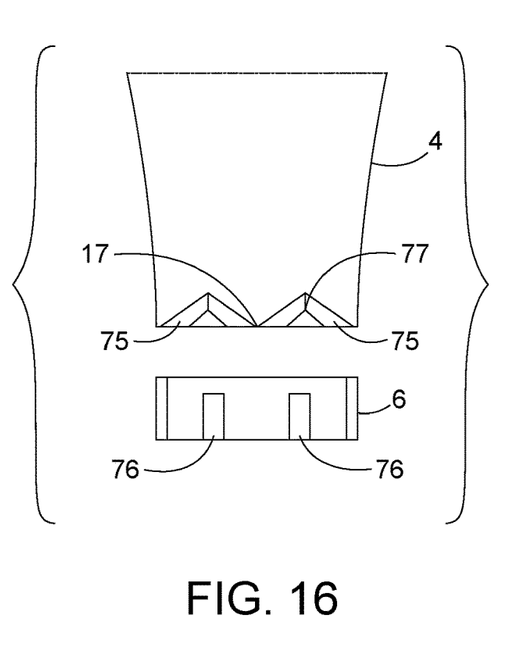
FIG. 16 is a schematic exploded view illustration of an alternative embodiment of a valve for the reservoir.

Alternatively, one or more duckbill valves can be used. With reference to FIG. 16, the bottom or floor 17 of the reservoir 4 is provided with one or more duckbill valves 75. A duckbill valve is known in the art and is designed to normally allow flow in one direction. At the top or tip of each duckbill valve 75 is an opening or slit 77, which is normally resiliently closed. When the reservoir 4 is seated in the support bracket 6 (see exploded view in FIG. 16), there is a hollow tube 76 fixed to the bottom of bracket 6 directly beneath each valve 75, which punches or stabs or forces its way through the resilient opening or slit 77 of the valve 75 when the reservoir 4 is pushed down and seated in bracket 6. The water in the reservoir 4 then flows into and through the tube 76 and out the bottom, onto the fragrance carrier or tablet 48. Alternatively, a vertical spike or prong with a plurality of outwardly extending vertical longitudinal ribs or fins (creating vertical and longitudinal drainage or flow channels) can be substituted for each tube 76. Other duckbill valves known in the art can be used.

Other valves can be used. For example, the rotatable flow regulator valve 64 of FIG. 14 can be mounted to the bottom of floor 17 of FIG. 15 so that the flow of the water released by the poppet valve 71 can be regulated. Also, with reference to FIG. 15, duckbill valves 75 can be provided on/through floor 17 and corresponding hollow tubes 76 can be mounted on crosspiece 74 (which can be larger and perforated). Also, with reference to FIG. 16, a plurality of duckbill valves 75 can be provided, with some being taller, some being shorter and others of in-between heights; and/or a plurality of hollow tubes (such as tubes 76) can be provided, of same or different heights. When the reservoir 4 is in a first orientation (i.e., facing "noon"), all or most of the tubes open all or most of the valves; in a second orientation (i.e., facing "3 PM"), only some of the tubes open some of the valves; in a third orientation (i.e., facing "6 PM"), none of the valves are opened. In this manner, volume of flow can be controlled. Other valves known in the art can be used to control or at least partially control flow from reservoir 4. The valves described above control or at least partially control the flow of water from the reservoir 4.

Figure 17:
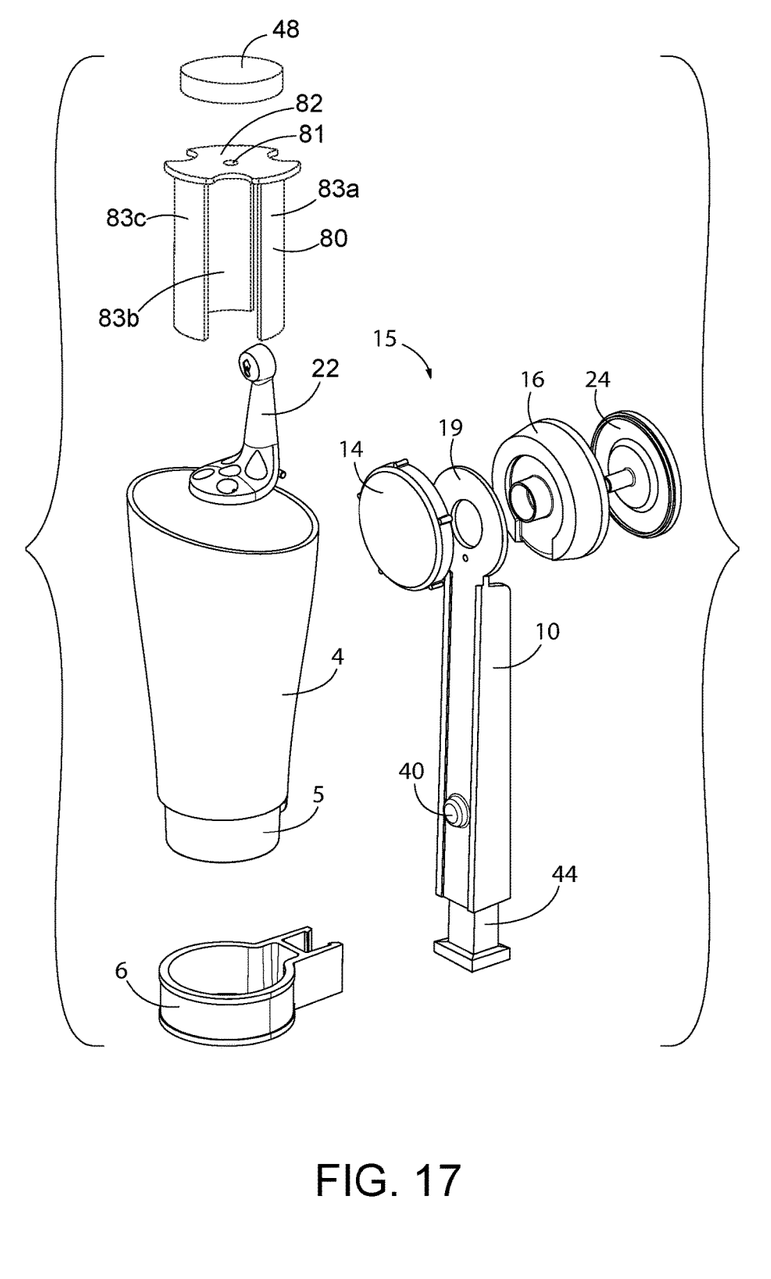
FIG. 17 is an exploded view illustrating an alternative embodiment of a fragrance carrier holder.
Figure 18:
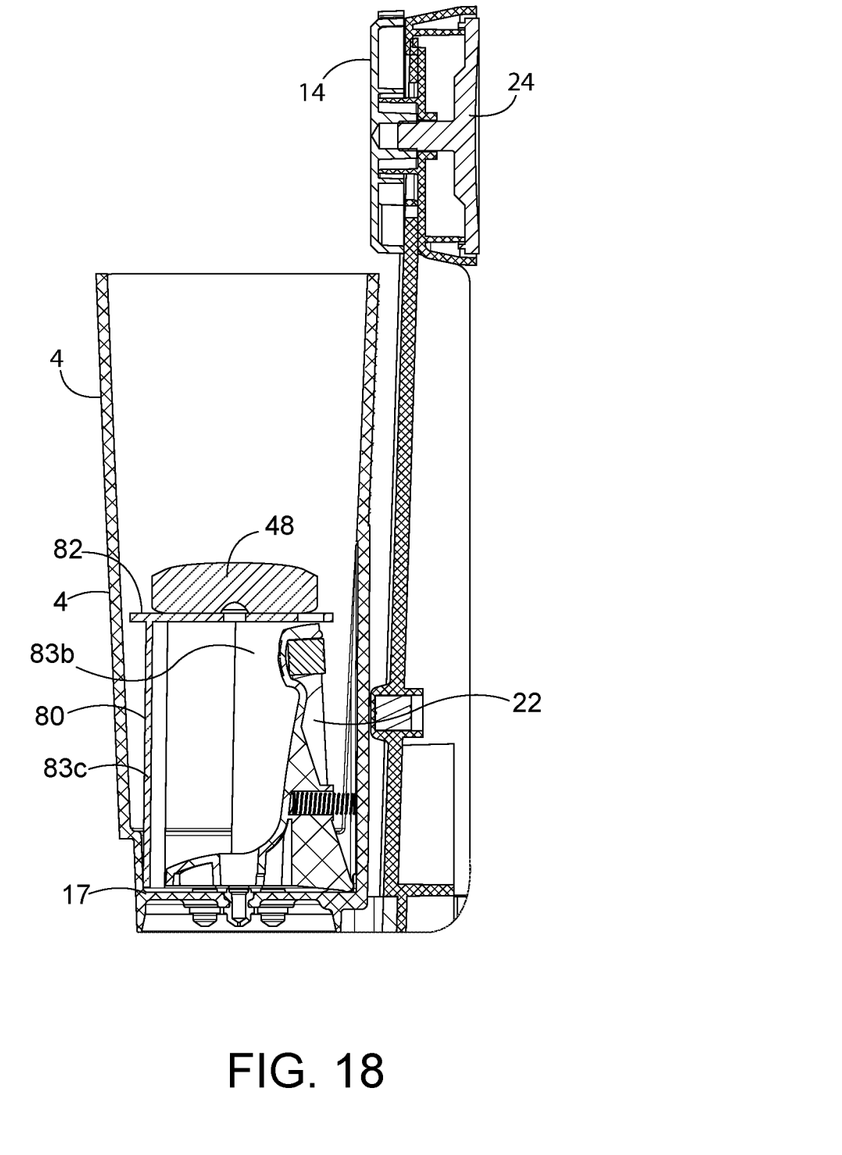
FIG. 18 is a cross-sectional view similar to FIG. 7 showing the fragrance carrier holder and shower tablet of FIG. 17 inside the reservoir.

With reference to FIGS. 17 and 18, there is shown a fragrance carrier holder 80 (which supports the fragrance carrier or tablet 48 off or above the floor 17) having a top shelf or shelf 82 (the top of which is optionally or preferably less than 1, 2, 3, 4, 5 or 6 cm above floor 17), three legs 83a, 83b and 83c and a drain hole 81. Optionally, a protrusion 50 can be provided in place of drain hole 81; optionally perforations like drain holes 62 can be provided in shelf 82. In use, fragrance carrier holder 80 is seated on floor 17 (FIG. 18) straddling around valve 22; fragrance carrier or tablet 48 is placed or dropped onto shelf 82 before or after reservoir 4 is filled with water; tablet 48 is immersed in the water; the reservoir 4 is seated in bracket 10 so that the valve (such as valve 22) is opened; the fragrance carrier or tablet 48 dissolves in the water and the water flows out the bottom of the reservoir 4. Alternatively, there can be no valve and bottom or floor 17 can just have nozzles 20 or drain openings or drain holes like drain holes 62, or floor 17 can have no nozzles or drain holes or openings, in which case the water does not flow out—in this case, after the fragrance carrier or tablet 48 has dissolved on the shelf 82 the user grabs reservoir 4 and empties or pours its water onto the shower floor or into the bathtub, etc.

Alternatively, the apparatus 2 can have no fragrance carrier holder, inside or outside. In this embodiment, the fragrance carrier or tablet 48 is dropped into reservoir 4 and the valve opens as usual. Alternatively, there can be no valve but there can be openings such as nozzles or holes 62; alternatively, there can be no valve or openings; in this case, after the fragrance carrier or tablet 48 is put in and dissolves, the user empties the water out of the reservoir 4.

Although the hereinabove described embodiments of the invention constitute the preferred embodiments, it should be understood that modifications can be made thereto without departing from the scope of the invention as set forth in the appended claims.

What is claimed is:

1. An apparatus for dissolving a fragrance carrier, the apparatus comprising a mount bracket, a water-holding reservoir and a fragrance carrier holder, the water-holding reservoir being supported by the mount bracket, the fragrance carrier holder being provided in association with the water-holding reservoir such that (a) water in the water-holding reservoir can contact and dissolve a fragrance carrier located on the fragrance carrier holder, the fragrance carrier holder being located inside the water-holding reservoir, or (b) water can flow from the water-holding reservoir to contact and dissolve a fragrance carrier located on the fragrance carrier holder, the apparatus being configured and adapted so that it is attachable to a vertical wall of a shower stall by suction or adhesive.

2. The apparatus of claim 1, wherein the fragrance carrier holder is provided outside the water-holding reservoir such that water can flow from the water-holding reservoir to contact and dissolve a fragrance carrier located on the fragrance carrier holder.

3. The apparatus of claim 2, wherein the fragrance carrier holder is supported by the mount bracket and wherein the fragrance carrier holder is located such that a fragrance carrier located on the fragrance carrier holder will be located beneath the water-holding reservoir.

4. The apparatus of claim 1, wherein the fragrance carrier holder is located inside the water-holding reservoir.

5. The apparatus of claim 1, wherein a plurality of nozzles are provided at a floor of the water-holding reservoir.

6. The apparatus of claim 1, wherein a wall mount is provided at an upper portion of the mount bracket.

7. The apparatus of claim 1, wherein the mount bracket comprises a reservoir support bracket which supports the water-holding reservoir.

8. The apparatus of claim 1, wherein the mount bracket comprises a fragrance carrier holder support bracket which supports the fragrance carrier holder.

9. The apparatus of claim 1, wherein a floor or shelf of the fragrance carrier holder is provided with a central protrusion.

10. The apparatus of claim 1, wherein the fragrance carrier holder is provided with a plurality of standoffs or ribs.

11. The apparatus of claim 1, wherein the water-holding reservoir is provided with a valve.

12. The apparatus of claim 11, wherein the valve is effective to at least partially control flow of water from the water-holding reservoir and is selected from the group consisting of flapper valves, rotatable flow regulator valves, poppet valves and duckbill valves.

13. The apparatus of claim 12, wherein the valve is a flapper valve.

14. The apparatus of claim 13, wherein the flapper valve has a flapper foot and a first magnet and wherein a second magnet is provided with the mount bracket such that (1) when the water-holding reservoir is removed from the mount bracket, the flapper foot is biased in a closed position to prevent water from flowing out of the water-holding reservoir, and (2) when the water-holding reservoir is mounted in or on or with the mount bracket, magnetic attraction between the first and second magnets causes the flapper foot to go to an open position to permit water to flow out of the water-holding reservoir.

15. The apparatus of claim 13, wherein the flapper valve is spring biased.

16. The apparatus of claim 13, wherein the flapper valve has a flapper foot, wherein one or more drain holes are provided at a base of the flapper foot.

17. The apparatus of claim 1, where drain holes or openings are provided through a floor of the fragrance carrier holder.

18. The apparatus of claim 12, wherein the valve is a rotatable flow regulator valve.

19. The apparatus of claim 12, wherein the valve is a poppet valve.

20. The apparatus of claim 12, wherein the valve comprises one or more duckbill valves.

21. The apparatus of claim 1, wherein the mount bracket is provided with a wall mount, wherein the wall mount comprises an adhesive-coated surface effective to adhesively attach the wall mount to a vertical wall of a shower stall.

22. The apparatus of claim 14, wherein a resilient valve membrane is provided on a bottom of the flapper foot.

23. The apparatus of claim 1, wherein a shower tablet is located on the fragrance carrier holder.

24. The apparatus of claim 7, wherein the water-holding reservoir has a narrowed portion which engages the reservoir support bracket.

25. A method for dissolving a fragrance carrier in a shower or bathtub, comprising the following steps:
 a) providing a mount bracket mounted via suction or adhesive in a shower stall or in or above a bathtub;
 b) at least partially filling a water-holding reservoir with water;
 c) before or after said filling step, mounting the water-holding reservoir on or with said mount bracket;
 d) contacting a fragrance carrier with water in or from the water-holding reservoir until the fragrance carrier is at least substantially dissolved.

26. The method of claim 25, wherein the fragrance carrier is a shower tablet.

27. The method of claim 25, wherein the fragrance carrier is located on a fragrance carrier holder, wherein the fragrance carrier holder is provided outside the water-holding reservoir such that water can flow from the water-holding reservoir to contact and dissolve the fragrance carrier.

28. The method of claim 27, wherein a floor of the fragrance carrier holder is provided with a central protrusion.

29. The method of claim 25, wherein the water-holding reservoir is provided with a valve which is effective to at least partially control flow of water from the water-holding reservoir.

30. The method of claim 29, wherein the valve has a first magnet and wherein a second magnet is provided with the mount bracket such that (1) when the water-holding reservoir is removed from the mount bracket, the valve is biased in a closed position to prevent water from flowing out of the water-holding reservoir, and (2) when the water-holding reservoir is mounted on or with the mount bracket, magnetic attraction between the first and second magnets causes the valve to go to an open position to permit water to flow out of the water-holding reservoir.

\* \* \* \* \*